United States Patent [19]

Cooley et al.

[11] Patent Number: 4,670,392
[45] Date of Patent: * Jun. 2, 1987

[54] SUNFLOWER REGENERATION THROUGH EMBRYOGENESIS

[75] Inventors: Gloria L. Cooley, Menlo Park; Anne S. Wilcox, Los Altos, both of Calif.

[73] Assignee: Sungene Technologies Corporation, Palo Alto, Calif.

[*] Notice: The portion of the term of this patent subsequent to Jun. 2, 2004 has been disclaimed.

[21] Appl. No.: 635,177

[22] Filed: Jul. 27, 1984

[51] Int. Cl.$^4$ .......................... C12N 5/00; C12N 5/02
[52] U.S. Cl. .................................. 435/240; 435/241; 800/1
[58] Field of Search ..................... 435/240, 241; 800/1

[56] References Cited

U.S. PATENT DOCUMENTS 4,354,327  10/1982  Smeltzer et al. ..................... 47/58
4,552,844  11/1985  Everett ............................... 435/240

OTHER PUBLICATIONS

Radford et al, 1968, *Manual of the Vascular Flora of the Carolinas*, Univ. N.C., Press, p. 1117.
The Yearbook of Agriculture 1961, (plate), *U.S. Dept. Agriculture*.

*Primary Examiner*—Thomas G. Wiseman
*Assistant Examiner*—David T. Fox
*Attorney, Agent, or Firm*—Robbins & Laramie

[57] ABSTRACT

The present invention relates to the regeneration of sunflowers via embryogenesis. The process comprises the steps of:
(a) culturing tissue obtained from a sunflower plant on a first medium which comprises mineral salts, vitamins, amino acids, sucrose and a hormone in an amount sufficient to ensure embryogenic callus formation;
(b) subculturing said callus on a second medium which comprises mineral salts, vitamins, sucrose and a hormone in an amount sufficient to ensure embryo formation and germination of said embryo, and
(c) subculturing said embryo or said germinated embryo on a third medium which comprises mineral salts, vitamins and sucrose, whereby plants are obtained.

32 Claims, No Drawings

SUNFLOWER REGENERATION THROUGH EMBRYOGENESIS

BACKGROUND OF THE INVENTION

1. Field of the Invention

The present invention relates to a process for the regeneration of sunflower plants from cell or tissue culture through embryogenesis. More specifically, cells or tissues of sunflower plants are cultured to produce calli. The calli are then cultured to produce embryos which are further cultured to cause germination and plantlet development. The present invention also relates to the sunflower plants and seeds which are produced by this method.

2. Description of the Prior Art

Several methods have been described in the prior art which result in the regeneration of sunflower. All of these methods have involved the use of organogenesis. However, these methods do not appear to be very efficient, and only result in the formation of a few regenerated plants. In organogenesis, plant parts are cultured on a first medium to induce callus formation. The callus can then be transferred to a second medium to induce shoot formation. The shoots are then transferred to a third medium to induce root formation, at which point the regenerated plantlets (plants) can be transferred to soil.

One additional method has been described to produce sunflower plants from an embryo. This method has found use in producing plants from embryos which do not develop in the original plant itself, either because of embryo abortion or seed dormancy resulting from the hybridization of non-compatible species. This method is embryo culture, and has been described by Chandler and Beard in *The Sunflower*, pages 45–47 (August/September 1980) and *Crop Science* 23, 1004 (1983). This process involves the rescue of the embryo prior to abortion followed by maturation of the embryo and germination to form the plant.

In this process, young embryos were isolated 3 to 7 days after pollination. These embryos were usually less than 0.1 mm in diameter. The embryos were plated on a solid, growth medium which contained B5 salts, vitamins, amino acids, the auxin α-naphthalene acetic acid (NAA) at a concentration of 0.05 mg/l, and 12% sucrose. It was found that if 9% sucrose was utilized instead of 12% and 1.0 mg/l indoleacetic acid (IAA) was used instead of NAA, then the young embryos had a tendency to grow as undifferentiated callus instead of embryos. In addition, very young embryos also germinated prematurely on this latter medium.

After 1 to 2 weeks, the enlarged (2–6 mm in diameter) embryos were transferred to a liquid medium for germination of the embryos to plants. During the enlargement period, some of the embryos began root formation and pigment synthesis. The embryos were matured to the cotyledon stage in order to obtain plant formation. The liquid, germination medium contained B5 salts and 1% sucrose. After the embryo generated roots and a shoot, it was transplanted to soil.

The present invention is the first instance of obtaining sunflower plants, i.e., regenerating sunflowers, through the use of an embryogenic callus pathway. Sunflower plants and seeds are produced by this process. The sunflower plants resulting from this process may differ from the starting plant material as a result of somoclonal variation. The pathway is also useful in that it will enable the use of various selection processes to provide further variation. The plants which are produced can then be used in conventional breeding programs.

SUMMARY OF THE INVENTION

The present invention is directed to a process for regenerating sunflowers, particularly to regenerating cultivars of domestic sunflower, *Helianthus annus*. This process uses an embryogenic culture system. The process comprises the steps of inducing embryogenic callus formation on an induction medium from tissue of a sunflower plant, forming embryos on an embryo regeneration medium and germinating and growing the embryos on a growth medium.

More specifically, the present process comprises the steps of:

(a) culturing tissue obtained from a sunflower plant on a first medium which comprises mineral salts, vitamins, amino acids, sucrose and a hormone in an amount sufficient to ensure embryogenic callus formation;

(b) subculturing said callus on a second medium which comprises mineral salts, vitamins, sucrose and a hormone in an amount to ensure embryo formation and germination of said embryo, and (c) subculturing said embryo or said germinated embryo on a third medium which comprises mineral salts, vitamins and sucrose, whereby plants are obtained.

The source of tissue is preferably immature embryos from the HA 89 and RHA 274 cultivars of *Helianthus annus*. The first medium preferably contains modified B5 mineral salts, the vitamins and amino acids as described by Chandler and Beard, supra. The second medium preferably contains MS mineral salts and the vitamins described by Henderson et al, *Am. J. Botany* 39, 467 (1952) which have been modified. The third medium preferably contains MS mineral salts.

The preferred hormones are either 2,4-dichlorophenoxyacetic acid (2,4-D) or a mixture of abscisic acid (ABA) and 2,4-D in the first medium, and either indoleacetic acid (IAA) or a mixture of IAA and kinetin in the second medium.

DETAILED DESCRIPTION OF THE INVENTION

The present invention is directed to a process for regenerating sunflowers, especially the domestic sunflower *Helianthus annus*, via embryogenesis. In this process, embryos are obtained from tissue culture. They can be germinated in tissue culture, and placed in soil for growth to maturation. The present invention is also directed to sunflower plants obtained by this process and to seeds from these plants.

In general, the process comprises (a) culturing sunflower plant tissue on a first medium to produce calli, (b) culturing the calli on a second medium to produce embryos which can also germinate on this medium, and (c) culturing either the embryos or the germinated embryos on a third medium for plantlet development. After plantlets have been developed, they can be grown in soil.

The plant tissue which is preferred for use in the initiation of callus is the immature embryo. The immature embryos with pericarps are isolated from the sunflower heads when they are in the range of 0.1 to 2.0 mm, preferably 0.5 to 2.0 mm. The embryos are sterilized with bleach and rinsed with sterile water. The immature embryos are isolated from the pericarps and plated onto a preconditioning or callus induction medium, hereinafter referred to as the first medium.

The first medium comprises mineral salts, vitamins, amino acids, sucrose and a hormone in an amount sufficient for callus formation. The mineral salts comprise macroelements and microelements. The macroelements used in the first medium may be the following compounds: magnesium sulfate, calcium chloride, monosodium phosphate, potassium nitrate and ammonium sulfate. the microelements contained in this medium are: boric acid, manganese sulfate, zinc sulfate, sodium molybdate (VI), copper (II) sulfate, cobalt chloride, potassium iodide, iron (II) sufate and disodium ethylenediaminetetraacetic acid (EDTA). This combination of mineral salts is known in the art as the B5 mineral salts. In the first medium, the B5 mineral salts have been modified so that the medium contains less iron and EDTA than the standard B5 mineral salts. It is also preferred to use less copper and iodine. It is also possible to substitute ammonium citrate for the ammonium sulfate.

In this medium, the iron is chelated by the EDTA. Citric and can be utilized in place of EDTA as the chelating agent. In a preferred embodiment, chelated iron is added in preparing the medium rather than adding iron (II) sulfate and disodium-EDTA.

The preferred amounts of the macroelements and microelements which are used to prepare one liter of medium are as follows: 250 mg magnesium sulfate heptahydrate, 150 mg calcium chloride dihydrate, 150 mg monosodium phosphate monohydrate, 2500 mg potassium nitrate, 134 mg ammonium sulfate, 3 mg boric acid, 10 mg manganese sulfate monohydrate, 2 mg zinc sulfate heptahydrate, 0.25 mg sodium molybdate (VI) dihydrate, 0.0025 mg copper (II) sulfate pentahydrate, 0.025 mg cobalt chloride hexahydrate, 0.075 mg potassium iodide, 2.78 mg iron (II) sulfate heptahydrate, and 3.73 mg disodium-EDTA.

In a more preferred embodiment, the iron concentration is 0.20–3.25 mg/l, preferably 0.81 mg/l. This may be added to the medium in any of the forms described above.

The first medium also contains vitamins. The vitamins which are utilized include nicotinic acid, thiamine, pyridoxine and myo-inositol. The vitamins have been described by Chandler and Beard, supra. The preferred amounts of vitamins needed to prepare one liter of medium are: 1 mg nicotinic acid, 10 mg thiamine hydrochloride, 1 mg pyridoxine hydrochloride and 4000 mg myo-inositol. This combination of vitamins will be referred to as the Chandler vitamins.

The first medium further contains amio acids. The amino acids are: alanine, glutamine, serine, tryptophan and cysteine. All amino acids are in the L-form unless otherwise indicated. The amino acids have been described by Chandler and Beard, supra. The preferred amounts of amino acids used to prepare one liter of medium are: 1000 mg alanine, 800 mg glutamine, 160 mg serine, 50 mg tryptophan, and 10 mg cysteine. This combination of amino acids will be referred to as the Chandler amino acids.

The first medium also contains sucrose and a hormone. The sucrose is utilized in the amount of 7%–14%, with 12% being preferred. The hormone which may be utilized is either 2,4-D alone or a mixture of 2,4-D and ABA. 5.0–12.0 µM 2,4-D or 5.10–12.0 µM 2,4-D and 1.0–7.0 µM ABA are utilized. Preferably, 10 µM 2,4-D or 10 µM 2,4-D and 5 µM ABA are used. Agar is used to solidify the medium. A final concentration of 0.7% has been found to be satisfactory. The medium has a pH of 5.5–6.0 with a preferred pH of 5.8.

The medium is sterilized by autoclaving all components except the vitamins and amino acids which are sterilized via microporous membrane filtration.

The immature embryos are plated on the first medium and cultured in the dark for not more than 7 days. Generally, five to seven days of culturing can be utilized. During this time, the embryo undegoes dedifferentiation and callus formation.

After culturing the embryos on the first medium, the callus is transfered and subcultured on an embryo regeneration medium, hereinafter referred to as the second medium. The callus is subcultured on the second medium for 2 to 3 weeks in the light, with a photoperiod of 12 to 16 hours per day, preferably 16 hours per day. During this time, embryos are formed on the callus. In addition, some of the embryos may germinate during this time period.

The second medium comprises mineral salts, vitamins, sucrose and a hormone in an amount sufficient for embryo formation. The mineral salts comprise macroelements and microelements. The macroelements which are utilized in the second medium are: magnesium sulfate, calcium chloride, monopotassium phosphate, potassium nitrate and ammonium nitrate. The microelements contained in this medium are: boric acid, manganese sulfate, zinc sulfate, sodium molybdate (VI), copper (II) sulfate, cobalt chloride, potassium iodide, iron (II) sulfate and disodium-EDTA. This combination of mineral salts is known in the art as the MS mineral salts.

The preferred amounts of the macroelements and microelements which are used to prepare one liter of medium are: 370 mg magnesium sulfate heptahydrate, 440 mg calcium chloride dihydrate, 170 mg monopotassium phosphate, 1900 mg potassium nitrate, 1650 mg ammonium nitrate, 6.2 mg boric acid, 16.9 mg manganese sulfate monohydrate, 8.6 mg zinc sulfate heptahydrate, 0.25 mg sodium molybdate (VI) dihydrate, 0.025 mg copper (II) sulfate pentahydrate, 0.025 mg cobalt chloride hexahydrate, 0.83 mg potassium iodide, 27.8 mg iron (II) sulfate heptahydrate, and 37.3 mg disodium-EDTA.

The second medium further contains vitamins. The vitamins which are present in this medium include thiamine, pyridoxine, myo-inositol, riboflavin, pantotthenate, p-aminobenzoic acid, niacin, choline, folic acid and biotin. These vitamins have been described by Henderson et al, supra. The preferred amounts of the vitamins used to prepare one liter of medium are: 0.5 mg thiamine hydrochloride, 0.1 mg pyridoxine hydrochloride, 100.5 mg myo-inositol, 0.05 mg riboflavin, 0.8 mg calcium pantotthenate, 0.25 mg p-aminobenzoic acid, 0.5 mg niacin, 0.1 mg choline hydrochloride, 0.1 mg folic acid, and 0.005 mg biotin. This combination of vitamins will be referred to as the Henderson vitamins, which have been modified to contain 100 mg/l more myo-inositol and 0.4 mg/l more thiamine hydrochloride.

The second medium also contains sucrose and a hormone. The sucrose is utilized in the amount of 2%–4%, with 3% being preferred. The hormone which may be utilized is either IAA or a mixture of IAA and kinetin. The hormone IAA is utilized in an amount of 0.05–1.0 µM, with 0.1 mM being preferred. Alternatively, a mixture of 0.05–2.0 µM IAA and 0.1–2.0 µM kinetin can be used. In this instance, it is preferred to use 0.1

μM IAA and 0.1 μM kinetin. Agar is added to the medium to solidify it. A concentration of 0.7% is satisfactory for this purpose. The medium has a pH of 5.5–6.0, with 5.8 preferred. The medium is sterilized as described above.

The embryos or germinated embryos are transferred from the second medium 2 to 3 weeks after the callus was transferred to the medium. During the culturing on the second medium, embryos are continuously formed. The early-formed embryos will often germinate prior to transfer to the third medium. The embryos or germinated embryos are subcultured on a plantlet development medium, hereinafter referred to as the third medium. The embryos or germinated embryos are subcultured on this medium for 1 to 2 weeks in the light, with a photoperiod of 12 to 16 hours per day, preferably 16 hours per day.

The third medium comprises mineral salts, vitamins and sucrose. The mineral salts comprise macroelements and microelements. The macroelements and microelements are as described for the second medium. The vitamins are myo-inositol and thiamine which are preferably present at 100 mg/l myo-inositol and 0.4 mg/l thiamine hydrochloride. The sucrose concentration is 2%–3%, with 3% being preferrred. Agar is added to the medium to solidify it. A concentration of 0.7% is satisfactory for this purpose. The third medium is sterilized by autoclaving, and has a pH of 5.5–6.0, with a preferred pH of 5.8.

After secondary leaves have appeared on the plantlets, the plantlets can be transferred to soil and the greenhouse. This is generally accomplished by transferring the plantlets to soil which is well moistened and contained in a high humidity chamber. Once the plantlets are established, they are removed from the high humidity chamber, transplanted to soil, and grown to maturity. Seeds are produced by the mature plants.

The above process is useful for regenerating plantlets from tissue of many cultivars of domestic sunflower. The process is especially useful for regenerating plantlets from *Helianthus annus* cv. HA 89 and RHA 274.

The present invention will be further described by reference to the following non-limiting examples. When the materials are cultured in the light, it is understood to mean light having a photoperiod of 16 hours per day, and at a temperature of 25°–29° C., unless indicated otherwise.

EXAMPLE 1

Preparation of Stock Solutions

1. Mineral Salts
   A. Modified B5

A 10X modified B5 mineral salts stock solution was prepared by dissolving the following ingredients in 1000 ml of distilled, deionized water.

| Component | Weight (mg) | Component | Weight (mg) |
| --- | --- | --- | --- |
| $MgSO_4.7H_2O$ | 2500 | $ZnSO_4.7H_2O$ | 20 |
| $CaCl_2.2H_2O$ | 1500 | $Na_2MoO_4.2H_2O$ | 2.5 |
| $NaH_2PO_4.H_2O$ | 1500 | $CuSO_4.5H_2O$ | 0.025 |
| $KNO_3$ | 25000 | $CoCl_2.6H_2O$ | 0.25 |
| $(NH_4)_2SO_4$ | 1340 | KI | 0.75 |
| $H_3BO_3$ | 30 | $FeSO_4.7H_2O$ | 27.8 |
| $MnSO_4.H_2O$ | 100 | $Na_2$ EDTA | 37.3 | the stock solution was divided into 100 ml aliquots.

2. Vitamins and Amino Acids

A. Chandler Vitamins and Amino Acids

A 40X stock solution of Chandler vitamins and amino acids was first prepared by dissolving the following components in 500 ml of distilled, deionized water.

| Component | Weight (g) | Component | Weight (g) |
| --- | --- | --- | --- |
| nicotinic acid | 0.02 | glutamine | 16 |
| thiamine.HCl | 0.2 | serine | 3.2 |
| pyridoxine.HCl | 0.02 | tryptophan | 1.0 |
| myo-inositol | 80 | cysteine | 0.2 |
| alanine | 20 | | |

This solution was sterilized by membrane filtration using a 0.2μ Gelman filter prior to addition to the first medium.

B. Henderson Vitamins

A 100X stock solution of Henderson vitamins (unmodified) was prepared by dissolving the following components in 200 ml of distilled, deionized water.

| Component | Weight (mg) | Component | Weight (mg) |
| --- | --- | --- | --- |
| thiamine.HCl | 20 | p-amino-benzoic acid | 10 |
| pyridoxine.HCl | 20 | niacin | 100 |
| myo-inositol | 100 | choline.HCl | 20 |
| riboflavin | 10 | folic acid | 20 |
| Ca pantothenate | 160 | biotin | 1 |

This solution was sterilized by membrane filtration prior to use as described above.

3. Hormones

A. 1 mM stock solution of 2,4-D was prepared by dissolving 0.1105 g of 2,4-D in a couple ml of 1M KOH and diluting to 500 ml with distilled, deionized water.

B. A 2 mM stock solution of IAA was prepared by dissolving 0.0876 g of IAA in a couple ml of 1M KOH and diluting to 250 ml with distilled, deionized water.

C. A 1 mM stock solution of kinetin was prepared by dissolving 0.108 g of kinetin in a couple ml of 1M HCl and diluting to 500 ml with distilled, deionized water.

D. A 1 mM stock solution of ABA was prepared by dissolving 0.132 g of ABA in a couple ml of 1M KOH and diluting to 500 ml with distilled, deionized water.

EXAMPLE 2

Preparation of Media

A. First Medium or Callus Induction Medium

The first medium was prepared by adding 10 ml of the 2,4-D stock solution, 120 g of sucrose and 7 g of agar to 100 ml of the modified B5 stock solution and the volume brought to 975 ml with distilled, deionized water. The pH was adjusted to 5.8 with 1M KOH and the mixture autoclaved at 120 psi for 15 minutes. 25 ml of the Chandler vitamins and amino acids stock solution, which had been sterilized as described above, was added to the cooling medium which was then poured into petri dishes.

To prepare first medium with a different concentration of 2,4-D, the appropriate amount of the 2,4-D stock solution was used. For example, to prepare a first medium having 5 μM, 2,4-D instead of 10 μM 2,4-D, 5 ml of the 2,4-D stock solution was used.

To prepare first medium with a mixture of 2,4-D and ABA, the appropriate amounts of each stock solution were used. For example, 10 ml of the 2,4-D stock solution and 5 ml of the ABA stock solution were used to prepare first medium containing 10 μM 2,4-D and 5 μM ABA.

B. Second Medium or Embryo Regeneration Medium

The second medium was prepared by dissolving one packet of powdered Murashige minimal organics medium without sucrose (obtained from Gibco Laboratories which contains the MS mineral salts, 100 mg myo-inositol and 0.4 mg thiamine hydrochloride), 30 g of sucrose and 7 g agar in 500 ml of distilled, deionized water. 0.05 ml of the IAA stock solution was then added, and the volume brought to 999 ml with distilled, deionized water. The pH was adjusted to 5.8 with 1M KOH and the mixture, autoclaved at 120 psi for 15 minutes. 1 ml of the Henderson vitamins stock solution, sterilized as described above, was added to the cooling medium. The mixture was then poured into petri dishes.

The procedure described above was utilized to prepare second medium having a different IAA concentration. To prepare second medium having a mixture of IAA and kinetin, the appropriate amounts of each stock solution were used. For example, 0.05 ml of the IAA stock solution and 0.1 ml of the kinetin stock solution were used to prepare second medium containing 0.1 μM IAA and 0.1 μM kinetin.

C. Third Medium or Plantlet Development Medium

The third medium was prepared by dissolving one packet of powdered Murashige minimal organics medium without sucrose, 20 g of sucrose and 7 g of agar in 1000 ml of distilled, deionized water. The pH was adjusted to 5.8 with 1M KOH. The mixture was autoclaved at 120 psi for 15 minutes. The cooling medium was poured into petri dishes.

EXAMPLE 3

Sunflower Regeneration

Immature embryos with pericarps were isolated from the head of the sunflower *Heliantthus annus* cv. RHA 274 when they were 0.5 to 2 mm in size. RHA 274 was obtained from Sigco Research, Incorporated. The embryos with pericarps were sterilized with a 20% bleach solution for 10 minutes. They were then rinsed with sterile water. The immature embryos were separated from the pericarps, endosperm and embryo sacs and plated onto the first medium, contained in a petri dish. The first medium was prepared as described in the preceding example, using 10 μM 2,4-D as the hormone. The petri dish was placed in the dark and cultured for 7 days to form calli.

At this time, each callus was transferred to the second medium, which was prepared as described above using 0.1 μM IAA as the hormone, and also contained in a petri dish. The callus was cultured on this medium for 21 days in the light. The callus differentiated to form embryos, and some of the embryos germinated.

The embryos and germinated embryos were then transferred to the third medium contained in petri dishes. The third medium was prepared as described above. The embryos were cultured on this medium for 14 days in the light. During this time period, the embryos germinated and produced plantlets, and the germinated embryos further developed to form plantlets.

After secondary leaves had appeared on the plantlets, the plantlets were transferred to soil in the greenhouse. The plantlets were planted in cubes, and the soil was well moistened. The cubes were placed in a sweater box and covered with a second sweater box to maintain a high humidity environment. The soil was kept well moistened for 5 days, after which the plantlets were transferred to 12 inch pots. The pots were watered three times weekly and fertilized every 10 days. The plants were hand-pollinated, and maintained until the seeds were mature. Seeds were then harvested and stored for future use.

EXAMPLE 4-6

The above example was essentially followed with some variation in the culture periods using different cultivars, hormones, hormone concentrations and sucrose concentrations. When *Helianthus annus* cv. HA 89 was utilized, immature embryos were isolated when they were 0.1-2.0 mm in size. HA 89 was also obtained from Sigco Research, Incorporated.

| Example | Cultivar | Sucrose (1st Med) | 1st Medium 2,4-D | 1st Medium ABA | 2nd Medium IAA | 2nd Medium Kinetin |
|---------|----------|-------------------|------------------|----------------|----------------|--------------------|
| 4 | HA 89 | 12% | 5 | | 0.1 | |
| 5 | HA 89 | 12% | 10 | | 0.5 | |
| 6 | HA 89 | 9% | 10 | | 0.5 | |
| 7 | RHA 274 | 12% | 10 | 5 | 0.1 | |
| 8 | RHA 274 | 9% | 10 | 1 | 0.5 | |
| 9 | RHA 274 | 12% | 5 | 2 | 0.1 | |
| 10 | RHA 274 | 12% | 5 | 5 | 0.5 | |
| 11 | HA 89 | 12% | 7 | | 0.3 | 0.5 |
| 12 | RHA 274 | 12% | 8 | 3 | 0.1 | 0.1 |
| 13 | RHA 274 | 12% | 5 | 7 | 1.0 | 1.0 |
| 14 | RHA 274 | 12% | 12 | | 1.0 | |
| 15 | HA 89 | 12% | 10 | 1 | 1.0 | |
| 16 | HA 89 | 12% | 10 | 5 | 1.5 | 0.5 |

Some of the seeds from some of the HA 89 regenerants were planted and germinated to produce sunflower plants.

While the invention has been described in connection with specific embodiments thereof, it will be understood that it is capable of further modifications. This application is intended to cover any variations, uses or adaptations of the invention following, in general, the principles of the invention and including such departures from the present disclosure as come within known and customary practice within the art to which the invention pertains.

What is claimed is:

1. A process for regenerating sunflower plants from cell or tissue culture through embryogenesis which comprises the steps of:
   (a) culturing tissue obtained from a sunflower plant on a first medium which comprises mineral salts, vitamins, amino acids, sucrose and a hormone selected from the group consisting of 2,4-dichlorophenoxyacetic acid (2,4-D) and a mixture of 2,4-D and abscisic acid (ABA) in an amount sufficient to ensure embryogenic callus formation;
   (b) subculturing said callus on a second medium which comprises mineral salts, vitamins, sucrose and a hormone selected from the group consisting of indoleacetic acid (IAA) and a mixture of IAA and kinetin, in an amount sufficient to ensure embryo formation and germination of said embryo, and
   (c) subculturing said embryo or said germinated embryo on a third medium which comprises mineral salts, vitamins and sucrose, whereby plants are obtained.

2. The process of claim 1 wherein said tissue is immature embryos.

3. The process of claim 1 wherein the concentrations of the hormones are:
 (1) 5.0–12.0 μM 2,4-D or 5.0–12.0 μM 2,4-D and 1.0–7.0 μM ABA in said first medium, and
 (2) 0.05–1.0 μM IAA or 0.05–2.0 μM IAA and 0.1–2.0 μM kinetin.

4. The process of claim 3 wherein the concentration of the sucrose is (1) 7%–14% in said first medium; (2) 2%–4% in said second medium; and (3) 2%–3% in said third medium.

5. The proces of claim 4 wherein said mineral salts of said first medium comprise magnesium sulfate, calcium chloride, monosodium phosphate, potassium nitrate, ammonium sulfate, boric acid, manganese sulfate, zinc sulfate, sodium molybdate, copper sulfate, cobalt chloride, potassium iodide and chelated iron.

6. The process of claim 5 wherein said mineral salts are the B5 mineral salts modified so that the concentration of the copper sulfate is 0.0025 mg/l and the concentration of the potassium iodide is 0.075 mg/l and the chelated iron contains 0.81 mg/l iron.

7. The process of claim 4 wherein said vitamins of said first medium comprise nicotinic acid, thiamine, pyridoxine and myo-inositol.

8. The process of claim 7 wherein said vitamins are the Chandler vitamins.

9. The process of claim 4 wherein said amino acids of said first medium are alanine, glutamine, serine, tryptophan and cysteine.

10. The process of claim 9 wherein said amino acids are the Chandler amino acids.

11. The process of claim 4 wherein said mineral salts of said second and third medium comprise magnesium sulfate, calcium chloride, monopotassium phosphate, potassium nitrate, ammonium nitrate, boric acid, manganese sulfate, zinc sulfate, sodium molybdate, copper sulfate, cobalt chloride, potassium iodide, iron sulfate and disodium-EDTA.

12. The process of claim 11 wherein said mineral salts are the MS mineral salts.

13. The process of claim 4 wherein said vitamins of said second medium are thiamine, pyridoxine, myo-inositol, riboflavin, calcium pantothenate, p-aminobenzoic acid, niacin, choline and folic acid.

14. The process of claim 13 wherein said vitamins are the Henderson vitamins modified to contain 100.5 mg/l myo-inositol and 0.5 mg/l thiamine hydrochloride.

15. The process of claim 6 wherein ammonium citrate is substituted for ammonium sulfate.

16. The process of claim 4 wherein said vitamins of said third medium are myo-inositol and thiamine.

17. A process for regenerating sunflower plants from cell or tissue culture through embryogenesis which comprises the steps of:
 (a) culturing tissue obtained from a sunflower plant on a first medium which comprises mineral salts consisting of magnesium sulfate, calcium chloride, monosodium phosphate, potassium nitrate, ammonium sulfate, boric acid, manganese sulfate, zinc sulfate, sodium molybdate, copper sulfate, cobalt chloride, potassium iodide and chelated iron, vitamins consisting of nicotinic acid, thiamine, pyridoxine and myo-inositol, amino acids consisting of alanine, glutamine, serine, tryptophan and cysteine, sucrose and a hormone selected from the group consisting of 2,4-dichlorophenoxyacetic acid (2,4-D) and a mixture of 2,4-D and abscisic acid (ABA) in an amount sufficient to ensure embryogenic callus formation;
 (b) subculturing said callus on a second medium which comprises mineral salts consisting of magnesium sulfate, calcium chloride, monopotassium phosphate, potassium nitrate, ammonium nitrate, boric acid, manganese sulfate, zinc sulfate, sodium molybdate, copper sulfate, cobalt chloride, potassium iodide, iron sulfate and disodium-EDTA, vitamins consisting of thiamine, pyridoxine, myo-inositol, riboflavin, calcium pantothenate, p-aminobenzoic acid, niacin, chloline and folic acid, sucrose and a hormone selected from the group consisting of indoleacetic acid (IAA) and a mixture of IAA and kinetin in an amount sufficient to ensure embryo formation and germination of said embryo, and
 (c) subculturing said embryo or said germinated embryo on a third medium which comprises mineral salts consisting of magnesium sulfate, calcium chloride, monopotassium phosphate, potassium nitrate, ammonium nitrate, boric acid, manganese sulfate, zinc sulfate, sodium molybdate, copper sulfate, cobalt chloride, potassium iodide, iron sulfate and disodium-EDTA, vitamins consisting of myo-inositol and thiamine, and sucrose, whereby plants are obtained.

18. The process of claim 17 wherein said tissue is immature embryos.

19. The process of claim 17 wherein the concentrations of the hormone are:
 (1) 5.0–12.0 μM 2,4-D or 5.0–12.0 μM 2,4-D and 1.0–7.0 μM ABA in said first medium, and
 (2) 0.05–1.0 μM IAA or 0.05–2.0 μM IAA and 0.1–20 μM kinetin.

20. The process of claim 19 wherein the concentration of sucrose is: (1) 7%–14% in said first medium; (2) 2%–4% in said second medium; and (3) 2%–3% in said third medium.

21. The process of claim 20 wherein said mineral salts of said first medium are the B5 mineral salts modified so that the concentration of the copper sulfate is 0.0025 mg/l and the concentration of the potassium iodide is 0.075 mg/l and the chelated iron contains 0.81 mg/l iron.

22. The process of claim 20 wherein said vitamins of said first medium are Chandler vitamins.

23. The process of claim 20 wherein said amino acids of said first medium are Chandler amino acids.

24. The process of claim 20 wherein said mineral salts of said second and third media are MS mineral salts.

25. The process of claim 20 wherein said vitamins of said second medium are Henderson vitamins, modified to contain 100.5 mg/l myo-inositol and 0.5 mg/l thiamine hydrochloride.

26. The process of claim 21 wherein ammonium citrate is substituted for the ammonium sulfate.

27. The process of claim 20 wherein the concentration of myo-inositol is 100 mg/l and of thiamine hydrochloride is 0.4 mg/l in said third medium.

28. A process for regenerating sunflower plants from cell or tissue culture through embryogenesis which comprises the steps of:
 (a) culturing tissue obtained from a sunflower plant on a first medium which comprises the B5 mineral salts modified so that the concentration of the copper sulfate is 0.0025 mg/l and concentration of the potassium iodide is 0.075 mg/l and the chelated iron contains 0.81 mg/l iron, the Chandler vitamins, the Chandler amino acids, 7%–14% sucrose and a hormone selected from the group consisting of 5–12 μM 2,4-dichlorophenoxyacetic acid (2,4-D) or a mixture of 1.0∝7.0 μM abscisic acid (ABA) and 5.10–12.0 μM 2,4-D to ensure embryogenic callus formation;

(b) subculturing said callus on a second medium which comprises the MS mineral salts, the Henderson vitamins modified to contain 100.5 mg/l myo-inositol and 0.5 mg/l thiamine hydrochloride, 2%–4% sucrose and a hormone selected from the group consisting of 0.05–1.0 μM indoleacetic acid (IAA) or a mixture of 0.05–2.0 μM IAA and 0.1–2.0 μM kinetin, to ensure embryo formation and germination of said embryo, and (c) subculturing said embryo or said germinated embryo on a third medium which comprises the MS mineral salts, 100 mg/l myo-inositol, 0.4 mg/l thiamine hydrochloride, and 2%–3% sucrose, whereby plants are obtained.

29. The process of claim 28 wherein said tissue is immature embryos.

30. The process of claim 28 wherein the concentration of sucrose is: (1) 12% in said first medium; (2) 3% in said second medium, and (3) 2% in said third medium.

31. The process of claim 28 wherein ammonium citrate is substituted for ammonium sulfate in the B5 mineral salts.

32. The process of claim 30 wherein the concentration of the hormones are:

(1) 10 μM 2,4-D or 10 μM 2,4-D and 5 μM ABA in said first medium, and (2) 0.1 μM IAA or 0.1 μM IAA and 0.1 μM kinetin in said second medium.

* * * * *